United States Patent [19]

Slightom

[11] Patent Number: 5,162,601
[45] Date of Patent: Nov. 10, 1992

[54] PLANT POTYVIRUS EXPRESSION VECTOR WITH A GENE FOR PROTEASE

[75] Inventor: Jerry L. Slightom, Kalamazoo, Mich.

[73] Assignee: The Upjohn Company, Kalamazoo, Mich.

[21] Appl. No.: 752,972

[22] Filed: Aug. 30, 1991

Related U.S. Application Data

[63] Continuation of Ser. No. 441,092, Nov. 22, 1989, abandoned.

[51] Int. Cl.$^5$ .................. A01H 1/04; C12N 15/00
[52] U.S. Cl. ...................... 800/205; 435/320.1; 935/25; 935/67
[58] Field of Search ............... 435/320.1, 252.3, 212; 800/205; 935/67, 25

[56] References Cited

PUBLICATIONS

Carrington et al. Proced. Nat'l Acad. Sci. 1988 vol. 85, 3391–3395.
Allison, R., et al., "The Nucleotide Sequence of the Coding Region of Tobacco Etch Virus Genomic RNA: Evidence for the synthesis of a Single Polyprotein", 1986, Virology 154:9–20.
Carrington, J. C., et al., "Small Nuclear Inclusion Protein Encoded by a Plant Potyvirus Genome is a Protease", 1987, J. Virology 61:2540–2548.
Dougherty, W. G., et al., "Nucleotide Sequence at the 3' Terminus of Pepper Mottle Virus Genomic RNA: Evidence for an Alternative Mode of Potyvirus Capsid Protein Gene Organization", 1985, Virology 146:282–291.
Dougherty, W. G., et al., "Biochemical and Mutational Analysis of Plant Virus Polyprotein Cleavage Site", 1988, Embo J. 7:1281–1287.
Dougherty, W. G., et al., "Expression and Function of Potyviral Gene Products", 1988, Ann. Rev. Phytopathol. 26:123–143.
Dougherty; W. G., et al., "Molecular Genetic Analysis of a Plant Virus Polyprotein Cleavage Site: A Model", 1989, Virology 171:356–364.
Dougherty, W. G., et al., "Molecular Genetic and Biochemical Evidence for the Involvement of the Heptapeptide Cleavage Sequence in Determining the Reaction Profile at Two Tobacco Etch Virus Cleavage Sites in Cell-Free Assays", 1989, Virology 172:145–155.
Dougherty, W. G., et al., "Characterization of the Catalytic Residues of the Tobacco Etch Virus 49-kDa Proteinase", 1989, Virology 172:302–310.
Yeh, S. D., et al., "Translation of Papaya Ringspot virus RNA in Vitro: Detection of a Possible Polyprotein That is Processed for Capsid Protein, Cylindrical-Inclusion Protein and Amorphous-Inclusion Protein", 1985, Virology 143:260–271.

Primary Examiner—Elizabeth C. Weimar
Assistant Examiner—Deborah Crouch
Attorney, Agent, or Firm—Mark Deluca

[57] ABSTRACT

The present invention relates to a recombinant multigene comprising a plurality of structural genes and a plurality of DNA sequences which encode peptide linkers. In the present invention, one of the structural genes encodes a protease, the DNA sequences encoding the peptide linkers are adjacent to the DNA sequences which encode the structural genes and the peptide linkers contain an amino acid sequence which the protease recognizes as a proteolytic cleavage site. The present invention additionally relates to transgenic plants which contain such a recombinant multigene transgene, host cells transformed with such a recombinant multigene, and transgenic animals which contain such a recombinant multigene transgene. Furthermore, the present invention relates to a method of producing a plurality of polypeptides in a host by incorporating and expressing in the host a such recombinant multigene.

8 Claims, No Drawings

PLANT POTYVIRUS EXPRESSION VECTOR WITH A GENE FOR PROTEASE

CROSS-REFERENCE TO RELATED APPLICATIONS

This application is a File Wrapper Continuation application of U.S. patent application Ser. No. 07/441,092 filed Nov. 22, 1989, abandoned.

FIELD OF INVENTION

The present invention relates to a recombinant DNA molecule useful in introducing genetic information into host organisms.

BACKGROUND OF THE INVENTION

The techniques of genetic engineering allow for the introduction of specific genetic information into a host regardless of the source of such information. Accordingly, it is possible to add foreign derived information to a host's genetic material. Moreover, it is possible to add additional copies of endogenous genetic material to a host. In either case, if the additionally provided genetic information introduced into the host is expressed, the result of such expression is to confer and/or enhance a desired trait or traits.

Expression of added genetic information in a host may be regulated by either endogenous regulatory elements or regulatory elements incorporated into the host with the added material. In order for expression of added genetic information to be controlled by endogenous regulatory elements, the added material must recombine with the host's genetic material in the correct orientation and at a location in the host's genetic material which contains such regulatory elements. Alternatively, the regulatory elements may be introduced into the host with the genetic material to be expressed.

Several genes may be added to a host, either simultaneously or at different times. If done simultaneously, the added material may be separate or linked. In all cases, in order for added genetic material to be expressed, it must be linked to regulatory genetic sequences which mediate gene expression.

It is more effecient, especially when adding more than one gene to a host, to link regulatory sequences to each gene rather than rely on use of endogenous regulatory sequences. In cases where the host is to provide the regulatory elements, the probability of correct integration of all added genes in each host cell is greatly reduced when more than one gene is sought to be incorporated since the requirements for functional integration operate independantly for each gene. If separate genes, each containing the necessary regulatory sequences are added to a host cell population, the probability of a cell being transformed by functioning copies of each desired genes is higher because the number of locations in the host cell's genetic material in which the added material can integrate is far greater.

When genetic information is added to a host, the cells which have incorporated the genetic material and are capable of expressing it must be selected. Selection of transformed host cells from the starting material host cell population can be a difficult task. If expression of the desired protein is not easily detected, a marker gene is usually added together with the gene sought to be expressed. The marker gene, with its own regulatory sequences, is usually linked to the desired gene to confirm the presence of the desired gene in selected cells.

The difficulties associated with selecting transformed host cells are compounded when if addition of more than one gene is performed and the desired genes are not linked to each other because different markers must be used to detect the presence of each new gene. When two genes are sought to be incorporated, this can be very inconvenient. When more than two genes are to be selected, this strategy becomes increasingly unfeasible.

One method used to overcome the difficulties of multiple selections is to link all the genes to each other. Using this approach, each gene is linked sequentially and a marker gene is additionally linked so that a single selection can be made to determine the presence of every gene. In order to proceed following this strategy, it is necessary to provide each linked gene with its own set of regulatory sequences. If each sequentially linked gene is to be equipped with its own set of regulatory sequences and each multiple gene construct additionally contains a marker gene with its own set of regulatory sequences, the size of the construct presents difficulties in both propagating the construction and transforming host cells with it.

The present invention overcomes the problems which are associated with incorporating more then one gene in an expressable form into a host cell by providing a multigene which is comprised of the several desired genes under the regulatory control of a single set of genetic regulatory elements. Thus, the multigene of the present invention is transcribed as a single polyprotein which must be processed subsequently in order to yield the substituent polypeptides.

Expression of genetic material to produce functional proteinaceous molecules generally requires several steps including post-translational modification of the gene product. In cases where the gene expressed is a multigene and therefore the gene product is a polyprotein, the translation product may be cleaved to form a plurality of polypeptides, each representing a desired product which may be functional with or without further modification.

Examples of translational products which are processed into a plurality of polypeptides are the polyproteins encoded by the genetic material of some viruses. These viruses contain a multigene which is expressed as a single gene under the control of a single set of regulatory elements. A single mRNA, generated from transcription of the multigene, is translated into a single polyprotein. The individual genes of the multigene are linked in series with intermediate linking sequences that encode an amino acid sequence which is a proteolytic cleavage site. Thus, the translated polyprotein contains a series of polpeptides which are connected to each other by proteolytic cleavage sites. The polyprotein is processed by an appropriate protease which cleaves the polyprotein at the cleavage sites and thereby severs the polyprotein into individual separate polypeptides. The protease which cleaves the polyprotein at the specific sites may be an endogenous protease or it may be a protease encoded by the viral genetic information.

The present invention provides a multigene which comprises a gene for a protease that recognizes the amino acid sequences encoded by the nucleotide sequences that link the individual genes of a multigene. Accordingly, the single translation product of the multigene is cleaved into the desired polypeptides. Using the present invention, it is possible to introduce a plurality of genes into a host without experiencing the problems associated with alternative methods. The genetic information which is incorporated into hosts using the present invention can be expressed and a plurality of polypeptides encoded therein may be produced.

INFORMATION DISCLOSURE

European patent application EP 0 223 452 describes plants that are resistant to viral diseases and methods for producing them. The process described comprises the steps of transforming a plant with a DNA insert comprising a promoter, a DNA sequence derived from the virus, and a poly(A) addition sequence.

PCT patent application PCT/US86/00514 refers to a method of conferring resistance to a parasite to a host of the parasite.

PCT International Patent Application No. PCT/US87/00396 published Sep. 11, 1987 discloses polyproteins and a method for constructing the same. According to the disclosure, polyproteins are constructed which are made up of individual proteins that have been joined together in a sequence whereby they retain their original biological activities and ability to interact with each other to perform multistep reactions in the proper sequential order. The present invention is distinguished from this disclosure in that this disclosure does not teach the presence of a protease but rather teaches away from the cleaving of the protein constituents of the polyprotein into functional subunits.

UK patent application GB 2141430-A published Dec. 19, 1984 discloses human calitonin gene-related peptide (CGRP) which is formed as part of a polyprotein that is specifically cleaved in vivo within the secretory pathway by proteolytic enzymes which recognize flanking basic amino acid residues. Further, the UK application discloses producing the calitonin gene-related peptide by expressing a fusion protein encoded by a gene construct which comprises the CGRP gene linked to a gene for a known protein. The peptide is linked to the protein through the linkage capable of selective chemical or enzymatic cleavage. The UK application does not teach or suggest including a protease as part of the polyprotein.

Allison et al. (1986) "The Nucleotide Sequence of the Coding Region of Tobacco Etch Virus Genomic RNA: Evidence for the Synthesis of a Single Polyprotein", Virology 154:9-20 describe the genome organization of the tobacco etch virus which is translated as a polyprotein.

Carrington, J. C. and Dougherty, W. G. (1987) "Small nuclear inclusion protein encoded by a plant potyvirus genome is a protease", J. Virology 61:2540-2548, disclose that the viral RNA multigene of tobacco etch virus encodes the 49K protease which is responsible for cleavage of the polyprotein produced when the viral RNA is translated.

Dougherty, W. G. et al. (1985) "Nucleotide Sequence at the 3' Terminus of Pepper Mottle Virus Genomic RNA: Evidence for an Alternative Mode of Potyvirus Capsid Protein Gene Organization", Virology 146:282-291, report the nucleotide sequence of the 3' terminus of the viral RNA genome of pepper mottle virus.

Dougherty, W. G. et al. (1988) "Biochemical and mutational analysis of plant virus polyprotein cleavage site", EMBO J. 7:1281-1287, describe the conservation of the proteolytic cleavage site among geographically distinct isolates of tobacco etch virus.

Dougherty, W. G. and Carrington, J. C. (1988) "Expression and function of potyviral gene products", Ann. Rev. Phytopathol. 26:123-143, describe potyviruses and some of the similarities the members of the group have with each another.

Dougherty, W. G. et al., Virology, 171:356-364 (1989) disclose that tobacco etch virus genome is expressed as a polyprotein which includes a 49 KD protease. This protease cleaves the polyprotein at five positions thereby produces six different proteins. The amino acid sequence which the protease recognizes and cleaves is disclosed.

Dougherty, W. G. and T. D. Parks, Virology, 172:145-155 (1989) disclose the relative rates of proteolytic cleavage by the 49 KD protease derived from tobacco etch virus. The rates of proteolytic cleavage at the different proteolytic cleavage sites on the polyprotein were compared.

Dougherty, W. G. et al., Virology, 172:302-310 (1989) report the effects of altering the amino acid sequence of the tobacco etch virus 49K protease on proteolysis by site directed mutagenesis of the protease cDNA gene. The findings disclosed suggest the catalytic triad of the protease to be composed of the $His^{234}$, $Asp^{269}$, and $Cys^{339}$.

Yeh and Gonsalves (1985) "Translation of Papaya Ringspot Virus RNA in vitro: Detection of a Possible Polyprotein That is Processed for Capsid Protein, Cylindrical-Inclusion Protein, and Amorphous-Inclusion Protein", Virology 143:260-271, describe the possibility that the RNA genome encodes a single proprotein which undergoes posttranslational processing to form the potyvirus protein products.

SUMMARY OF THE INVENTION

The present invention relates to a recombinant multigene comprising a plurality of structural genes and a plurality of DNA sequences which encode peptide linkers. In the present invention, one of the structural genes encodes a protease, the DNA sequences encoding the peptide linkers are adjacent to the DNA sequences which encode the structural genes and the peptide linkers contain an amino acid sequence which the protease recognizes as a proteolytic cleavage site.

The present invention additionally relates to transgenic plants which comprise such a recombinant multigene transgene. Furthermore, the present invention relates to host cells transformed with a recombinant multigene. Additionally, the present invention relates to transgenic animals which comprise a recombinant multigene transgene.

The present invention relates to a method of producing a plurality of polypeptides in a host by incorporating and expressing in the host a recombinant multigene comprising a plurality of structural genes which encode such polypeptides and a plurality of DNA sequences which encode peptide linkers between the structural genes. One structural gene encodes a protease which recognizes and cleaves the peptide linkers.

DETAILED DESCRIPTION OF THE INVENTION

Certain conventions are used in Charts 1-7 to illustrate plasmids and DNA fragments as follows:
(1) The single line figures represent both circular and linear double-stranded DNA.

(2) Asterisks (*) indicate that the molecule represented is circular. Lack of an asterisk indicates the molecule is linear.

(3) Dashes ( - - - ) indicate additional portions of the molecule represented which is omitted because it is irrelevant for the purpose of the Chart.

(4) Junctions between natural boundaries of functional components are indicated by vertical lines along the horizontal lines.

(5) Genes or functional components are indicated below the horizontal lines.

(6) Restriction sites are indicated above the horizontal lines.

(7) Distances between genes and restriction sites are not to scale. The figures show the relative positions only unless indicated otherwise.

(8) The following abbreviations are used to denote function and components:
P = Promoter;
I = Intergenic region including 5' untranslated and imitation codon according to Kozak's element;
Pro = Protease;
S = Polyadenylation signal;
$P_{ca}$ = CaMV 35S Promoter;
$I_{cm}$ = CMV intergenic region including 5' untranslated region and imitation codon according to Kozak's element;
$S_{ca}$ = CaMV polyadenylation signal;
$Pro_{tev}$ = TEV protease gene;
PSJ = Protease splice junction recognized by TEV protease;
NIP = TEV 54 Kdalton nuclear inclusion protein gene;
cp = Coat protein gene;
$TEV_{cp}$ = TEV coat protein gene;
$PRV_{cp}$ = PRV coat protein gene;
$P_{sv}$ = SV40 promoter;
HR = Human renin gene;
$H_{tPA}$ = Human tPA gene;
$S_{tPA}$ = Human tPA polyadenylation signal.
$P_L$ = λ phage $P_L$ promoter Many of the recombinant DNA methods employed in practicing the present invention are standard procedures, well known to those skilled in the art, and described in detail in, for example, European Patent Application Publication Number 223452 published Nov. 29, 1986, which is incorporated herein by reference. Enzymes are obtained from commercial sources and are used according to the vendor's recommendations or other variations known in the art. General references containing such standard techniques include the following: R. Wu, ed. (1979) Methods in Enzymology, Vol. 68; J. H. Miller (1972) Experiments in Molecular Genetics; T. Maniatis et al. (1982) Molecular Cloning: A Laboratory Manual; D. M. Glover, ed. (1985) DNA Cloning Vol. II; H. G. Polites and K. R. Marotti (1987) "A step-wise protocol for cDNA synthesis". Biotechniques 4:514–520; S. B. Gelvin and R. A. Schilperoort, eds. Introduction, Expression, and Analysis of Gene Products in Plants, all of which are incorporated by reference.

For the purposes of the present disclosure the following definitions for terms used herein are meant to apply.

"Expression cassette" means a DNA fragment which contains a gene operably linked to regulatory sequences necessary for gene expression.

"Promoter" means a promoter which is functional in the host.

"Operably linked" refers to the linking of nucleotide regions encoding specific genetic information such that the nucleotide regions are contiguous, the functionality of the region is preserved and will perform its function relative the the other regions as part of a functional unit.

"Vector" is a vehicle by means of which DNA fragments can be introduced into host organisms.

"Expression vector" is a vehicle by means of which DNA fragments that contain sufficient genetic information and can, therefore, be expressed by the host can be introduced into host organisms.

"Antipathogen gene" is a gene which encodes a DNA sequence which is either the antisense sequence of a pathogenic gene or the antipathogenic gene encodes a peptide whose presence in an organism confers an increased resistence to a pathogen.

"Multigene" means a DNA sequence containing the genetic information for more than one gene but expressed as a single unit under the regulatory control of one set of regulatory sequences.

"Structural genes" means genetic information which encodes a peptide molecule or the antisense strand of a gene or gene product.

"Peptide linkers" means amino acid residues which connect the polypeptide subunits of a polyprotein.

"Polyprotein" means the translation product of a multigene comprising polypeptide subunits connected by peptide linkers.

"Protease" means polypeptide enzyme which recognizes specific amino acid sequences and cleaves the peptide bond at such specific sequence.

"Proteolytic cleavage site" means the specific amino acid residue sequence recognized and cleaved by a protease.

"Protease splice junction" means the specific amino acid residue sequence recognized and cleaved by a protease.

The terms "proteolytic cleavage site" and "protease splice junction" are used herein to mean the same thing and are interchangeable.

"Antisense" means the complementary nucleic acid strand to the strand which contains the triplet coding sequence of a polypeptide.

The present invention relates to a recombinant multigene comprising a plurality of structural genes, one of which enclodes a protease, and a plurality of DNA sequences which encode peptide linkers which are adjacent to the DNA sequences which encode the structural genes and contain an amino acid sequence which the protease recognizes as a proteolytic cleavage site.

To practice the present invention, genes which are desired to be expressed are sequentially linked to form a polygene. The regulatory sequences are provided such that the polygene is transcribed and translated as a single unit. Thus, a single set of regulatory sequences are provided and the linked genes are expressed as a single polyprotein.

In addition to providing a series of sequentially linked desired genes which are transcribed and translated as a single unit, the gene for a protease must also be sequentially linked to the polygene. This protease gene is transcribed and translated by the same regulatory elements such that the protease protein is part of the polyprotein translation product.

Furthermore, according to the present invention, each gene of the polygene is linked by a nucleotide sequence that encodes an amino acid sequence which is a proteolytic cleavage site. Thus, in the polyprotein translation product, each of the linked polypeptides encoded by the plurality of genes of the polygene is connected to an adjacent polypeptide by an amino acid sequence that is cabale of being cleaved by a protease. Therefore, in the presence of the protease which recognizes the proteolytic cleavage site, the polyprotein will be cleaved by the protease into protein subunits.

According to the present invention, the protease gene provided in the polygene encodes the protease which recognizes and cleaves the amino acid sequence that connects the subunit proteins of the polyprotein to eachother. After the multigene is translated into the polyprotein, the protease may be cleaved from the polyprotein by a protease from a different protease molecule or it may autocleave itself from the polyprotein from which it is linked. It is not necessary that a protease molecule be severed from the polyprotein in order for it to function because it is possible that the functional portion of the polypeptide can be exposed and in correct conformation to recognize and cleave the proteolytic cleavage site.

Using techniques well known to those having ordinary skill in the art, a multigene according to the present invention may be constructed. To do so, it is necessary to obtain copies of the genes which encode the proteins desired to be introduced into the host. The regulatory sequences must not be present in the genes. It is, therefore, possible and desirable to use cDNA copies of genes desired to be expressed. The gene for a protease must also be obtained, preferably a cDNA copy of such a gene. The amino acid sequence which forms the proteolytic cleavage site that is recognized by the protease must be known and copies of the nucleotide sequence encoding the amino acid sequence must be constructed for use as linker sequences to connect the genes which make up the polygene. With these starting materials, one having ordinary skill in art could assemble the polygene by alternately linking genes and linkers.

Chart 1 depicts an example of a polygene without regulatory sequences. The polygene in Chart 1 contains a total of 5 genes including the protease gene but merely serves as an example of the order of assembly.

As shown in Chart 1, the subunits of the polygene are alternate sequences encoding desired proteins and proteolytic cleavage sites. In Chart 1 the protease is located at the 3' of the construction. This location at the 3' terminal is not necessary but serves only as an example of the arrangement of a polygene according to the present invention. The protease gene can be located anywhere on the polygene provided that when transcribed and then translated into a polyprotein, the protease portion of the polyprotein is capable of functioning to cleave peptides at the correct proteolytic cleavage sites.

When assembling multigenes, one having ordinary skill in the art can test construction for functioning proteases. To do so, one can follow the teachings Melton, D. A., et al. (1984), Nucl. Acids Res. Vol. 12, 18:7035-7056; Maniatis, T., et al. (1982), Molecular Cloning Manual; Palham and Jackson, Eur. J. Biochem. 67:247; and, Promega Biological Research Products 89/90 Catalog, p. 98-100, Promega, Madison, WI; and perform in vitro transcription and translation of the DNA multigene constructs. The material can then be run on PAGE gels. If the translation product apepars as a single band, the protease is not functioning. However, if the translation product appears as several bands, each the size of subunit polypeptides, the protease is active and the multigene functional.

Using the present invention, genetic information may be incorporated into a host cell, thereby conferring new and/or enhanced traits. The new or enhanced trait may be the production of the polypeptide itself or some other physical manifestation brought on by the production of such polypeptide. Thus, one application of these techniques is to create hosts which produce either greater quantities of endogenous proteins or produce heterologous proteins. In each case, the host can be a source of the desirable proteins which can be produced in large quantities and purified. Alternatively, production of the polypeptides encoded by the added genetic material may confer a desirable trait upon the host which is manifested through the presence and/or functioning of the polypeptide. Furthermore, the presence of an antisense strand of RNA can prevent production of undesirable polypeptides in a cell. In any case, it is the expression of the introduced genetic information which produces the desired result. Multigenes according to the present invention can be used in prokaryotic or eukaryotic including animal or plant systems depending on what type of regulatory sequences are provided. For example, a multigene according to the present invention may be used in E. coli or eukaryotic tissue culture expression systems or in the production of transgenic plants and animals. In each case, a plurality of genes may be expressed under the control of a single regulatory sequence and a plurality of polypeptides may be produced first as a polyprotein which is then processed into the individual desired gene products. Alternatively, the antisense sequence of undesirable genes may be produced which will prevent production of undesirable gene products.

DESCRIPTION OF THE PREFERRED EMBODIMENTS

Example 1

Construction of an expressible Multigene containing the Tobacco Etch Virus (TEV) protease genes and two potyvirus coat protein genes (TEV and PRV)

This example describes a method of assembling regulatory elements and known genes to produce an expressible multigene Polymerase Chain Reaction (PCR) technology is used in order to produce copies of the desired genetic sequences. Furthermore, desired restriction enzyme sites are added at both the 5' and 3' end of copies made. The techniques used are referred to as Custom Polymerase Chain Reaction (CPCR) to describe the PCR technique used to amplify genetic sequences and add custom restriction endonuclease sites at the 5' and 3' ends of such sequences.

This example describes production of a multigene which comprises the TEV protease gene, coat protein genes from both TEV and papaya ring spot virus II (PRV), as well as the necessary peptide linkers located between each of the structural genes referred to herein as protease splice junctions (PSJ). Additionally, this example describes providing a multigene with the necessary genetic regulatory elements to allow expression in a plant system. Accordingly, the final product of this example may be used to generate transgenic plants capable of expressing desired proteins, TEV and PRV coat proteins, and therefore, render such a transgenic plant resistance to viral infection by either TEV, PRV or both.

The following expression cassette was constructed to provide the necessary plant regulatory sequences a promoter (a 5'-untranslated region, a translation initiation codon, and a polyadenylation signal) to multigene inserts in order to achieve high level expression of the inserts in transgenic plants. The expression cassette, described in PCT patent application Serial Number PCT/US89/03095 filed Jul. 20, 1989, titled "Expression Cassette for Plants" incorporated herein by reference, may be used to express any multi-gene inserted therein. The expression cassette contains a constitutive promoter; a 5'-untranslated region which enhances gene expression; an initiation codon which comprises Kozak's Element; a cloning site where the multigene to be expressed may be inserted to produce a functional expression unit; and a 3'-untranslated region which comprises a poly(A) addition signal and untranslated flanking regions. More specifically, the expression cassette in the preferred embodiment of the present invention is found in the plasmid pUC18cp-exp and comprises the cauliflower mosaic virus (CaMV) 35S transcript promoter, the 5'-untranslated region of cucumber mosaic virus (CMV), the CMV translation initiation codon, and the CaMV polyadenylation signal. The plasmid pUC18cp-exp is shown in Chart 2.

As shown in Chart 2, the desired region from pUC18cp-exp includes the promoter from CaMV ($P_{ca}$); the intergenic region from CMV ($I_{cm}$) which includes the 5'-untranslated region and the initiation codon according to Kozak's Element; and the 3'-untranslated region including the polyadenylation signal from CaMV ($S_{ca}$). Using CPCR technology, oligomers were produced which amplify the expression cassette in pUC18-cp-exp and add XbaI restriction sites on the 5'-end of the $P_{ca}$ and 3'-end of $S_{ca}$. Accordingly, the desired portion of pUC18cp-exp may be produced having XbaI sites at both the 5' and 3' ends. The product of this reaction is referred to as cp-exp fragment. It may be treated with XbaI and cloned into the XbaI site of pUC18. The resulting plasmid is referred to as P18Xcp-exp and is shown in Chart 2. The following oligomer sequences can be used for this amplification:

5' primer 5'--ATCGATTTCTAGAGGAAACCTCCTCGGATTCCATTG--3'
and
3' primer 5'--ATCGATTTCTAGATACCACTGGATTTTGGTTTTAGG--3'

The protease gene from TEV including the endogenous PSJ 3' to the gene is then amplified using CPCR technology and inserted into pUC18Xcp-exp. The protease gene including the PSJ is made using CPCR technology and is provided with NcoI sites at the 5' and the 3' ends of the sequence so that it may be cloned into the NcoI site of pUC18Xcp-exp. Furthermore, the 3' oligomer primer used contains an inframe BglII site between the PSJ site between the PSJ and the NcoI site. The resulting product is referred to as TEV protease fragment. When the TEV protease fragment is inserted into pUC18Xcp-exp, the inframe BglII site will serve as the insertion point for desired structural genes. Two amino acids will be added to the N-terminus of the gene product of the inserted gene after the protease cleaves the polyprotein at the PSJ. Chart 2 depicts the region of the TEV genome which contains the protease gene and the PSJ. This region is upstream from the TEV 54 KD nuclear inclusion protein gene (NIP). Chart 2 also depicts the protease/PSJ region which is amplified which is referred to as TEV protease fragment. The following oligomers are used to produce TEV protease fragment:

5' primer 5'--ATCGATTCCATGGGGAAGAAGAATCAGAAGCACAAGC--3'
and
3' primer 5'--ATCGATTCCATGGAGATCTCTTCTCCCCTTGCGAGTACACC--3'.

The TEV protease fragment and pUC18Xcp-exp are both digested with NcoI. The products are ligated. The pUC18Xcp-exp with the TEV protease fragment inserted at the NcoI site is referred to as pUC18Pro-exp and shown in Chart 2.

CPCR technology is used to amplify copies of the desired structural protein genes. In this example, coat protein genes from TEV and PRV are produced this way. Using CPCR technology, the amplified regions can be provided with desired restriction enzyme sites at the 5' and 3' ends. Furthermore, since both TEV and PRV are potyviruses, each gene is provided with an endogenous PSJ recognized by the TEV protease. These PSJ's may be used in the construction. In this example, the PRV PSJ is retained.

Oligomers are designed to amplify the coat protein gene from the TEV genome. The 5' oligomer contains the BglII site and the 3'-oligomer contains a KpnI site. The 5' oligomer which adds the BglII site adds additional genetic information which results in the addition of two amino acid residues to the N-terminus by the TEV coat protein produced by expression of the gene. When cloned into the BglII site of pUC18pro-exp, the N-terminus of resulting TEV coat protein gene transcript contains an additional 5 amino acid residues total. Chart 3 depicts the portion of TEV which contains the coat protein as well as the amplified product which contains the restriction endonuclease site. This amplified product is referred to as TEV coat insert. Oligomers used to generate TEV coat insert are as follows:

5' primer 5'--ATCGATTGAGTCTAGTGGCACTGTGGATGCTGGTGC--3'
and
3' primer 5'--ATCGATTGGTACCCTGGCGGACCCCTAATAGTGTGTGC--3'.

CPCR technology is also used to amplify the coat protein gene from PVR. The endogenous PSJ located upstream from the coat protein is amplified together with the coat protein gene. To do so, oligomers are designed to provide an inframe KpnI site 7 amino acids upstream from the 5' end of the PSJ and the 3' oligomer provides a BglII site at the 3' end of the coat protein gene downstream from the translation termination codon (TAA). Chart 3 shows the relevant portion of the PRV genome which is amplified using CPCR as well as the amplified product which contains a KpnI site at the 5' end of the PSJ and a BglII site at the 3' end of the coat protein gene. This product is referred to as PRV coat insert. Oligomers used to generate PRV coat insert are as follows:

5' primer 5'--ATCAGTTGGTACCAATACGCATGTGTTTCATCAGTCCAAG--3'

Both the TEV coat insert and the PRV coat insert are digested with KpnI and gel purified. The two fragments are then ligated at the KpnI site to obtain the fused inframe TEV and PRV coat protein genes in a single fragment (about 1800 bp). Accordingly, the order of genetic information is: 1) the TEV coat protein gene; followed by 2) the PRV PSJ; followed by 3) the PRV coat protein gene. This ligated product has BglII sites at both the 5' and 3' ends. The ligated product is depicted in Chart 3 and referred to as TEV/PRV coat fragment.

The TEV/PRV coat fragment and pUC18pro-exp are then digested with BglII. The products are ligated and as a result, the TEV/PRV coat fragment is inserted into pUC18pro-exp at the BglII site. The orientation can be confirmed using restriction endonuclease mapping to ensure that the coat protein genes have been inserted in the correct orientation and are inframe with the protease gene. The resulting plasmid is referred to as pUC18TEVPRV and is depicted in Chart 3. The 3.7 KB insert containing the regulatory elements and the multigene construct can be removed by XbaI digestion and cloned into Agrobacterium vector, pGA482, for transfer into Agrobacterium strains followed by transfer into a plant genome. Expression of this construction followed by cleavage of the resulting polyprotein at the PSJ by the protease gene product yields a plant resistant to viral infection by both TEV and PRV. The method of transferring the 3.7 KB fragment into the Agrobacterium vector and the transfer into a plant genome are described in PCT patent application Serial Number PCT/US89/03095.

As depicted in Chart 3, the 3.7 kb fragment of pUC18TEVPRV can be isolated from the entire plasmid by XbaI digestion. This fragment can be inserted into the modified Agrobacterium-derived micro-vector pGA482 (Pharmacia LKB Biotechnology, Piscataway NJ) shown in Chart 9. Plasmid pGA482 is modified to include the addition of the β-glucuronidase gene at the XbaI site, generating a suitable micro-T-DNA vector which contains the necessary Agrobacterium T-DNA transfer signals to mediate transfer from an Agrobacterium and integration into a plant genome. The plasmid, pGA482/G/CPTEVPRV (shown in Chart 9) contains a wide-host range origin of replication for replication in Agrobacterium. This plasmid (or derivatives thereof) was transferred into virulent or non-virulent strains of *Agrobacterium tumefaciens* or *Agrobacterium rhizogenes.*

After transfer of the engineered plasmid pGA482/G/CPTEVPRV into Agrobacterium strains, the transformed Agrobacterium can be used to transfer and integrate within a plant genome the plant-expressible multigene construct contained within its T-DNA region. This transfer can be accomplished using the standard methods for T-DNA transfers which are known to those skilled in the art, or this transfer can be accomplished using the methods described in U.S. patent application Ser. No. 07/135,655 filed Dec. 21, 1987 entitled "Agrobacterium Mediated Transformation of Germinating Plant Seeds". These methods are described below.

The development of simple, non-tissue culture dependent methods for transfer, stable integration, and sexual transmission of genetic material into plant species is of great interest and importance. Reports from Graves and Goldman (1986) Plant Mol. Biol. 7:43-50 and Feldmann and Marks (1987) Mol. Gen. Gent. 208:1-9 present evidence that transformed whole plants can be obtained Agrobacterium-mediated transformation of the mesocotyl cells of germinating seeds.

The process described here represents an improvement of the Graves and Goldman (1986) technique for the transformation of the seeds of monocotyledous plants and its extension to dicotyledonous plants.

Germinating seeds were inoculated with either virulent or non-virulent *Agrobacterium tumefacien* or *Agrobacterium rhizogenes* strains which contain the binary plasmid PGA482 or their derivatives. The binary plasmids encode a plant expressible NPT II gene within its T-DNA region and derivatives of the plasmids additionally contain genes that will convey useful traits to transformed species. Most plants resulting from seeds inoculated with virulent Agrobacterium strains also contained the binary plasmid developed typical crown galls. However, NPT II activity was found in the leaves of some inoculated whole plants, indicating that the binary T-DNA region was also transferred. Transfer of the binary T-DNA region was also accomplished by using avirulent strains of *A. tumefaciens* or *A. rhizogenes.* Rates of transformation can be determined by the presence of NPT II enzyme activity.

Seeds of *Phaseolus vulgaris* cv. Olathe or *Glycine max* (cV.A0949) are surface sterilized with 15% Clorox for 10 minutes, followed by 4–5 rinses with distilled water and then placed on moistened paper towels in a temperature controlled Percival incubator at 28° C. and allowed to germinate for various times, 16 to 96 hours. Seed coats are removed and the decoated seeds are opened in halves (that is how cotyledons were removed from the main seed body). The mesocotyl region of the germinating seeds, with their plummule still attached, are infected with an overnight liquid culture of various Agrobacterium strains by using an Eppendorf pipetter fitted with a 27½ gauge needle. Seeds are infected with virulent or non-virulent *A. tumefaciens* strains (A208C58, C58z707 and A208/phas-zein) or *A. rhizogenes* strains (A4RS and A4RS(pR:B278b)pu3.3c-1]. The common *A. tumefaciens* and *A. rhizogenes* strains are available from ATCC, 12301 Parklawn Drive, Rockville, MD. The disarmed *A. rhizogenes* strain RS(pRiB278b) has been described by Vilaine and Casse-Debart (1987) Mol. Gen. Genet., 206,17 and is available from Dr. F. Casse-Delbart, C.N.R.A., Routede Saint Cyr, F78000, Versailles, France. The disarmed *A. tumefaciens*, strain C582707 is available from Dr. A. G. Hepburn, University of Illinois, Urbana, IL. Inoculated seeds are then placed on moistened paper towels in petri dishes and incubated at 28° C. After four days these seedlings are transformed to soil and grown to maturity in the greenhouse. Plants infected with virulent strains of *A. tumefaciens* are scored for efficiency of gall formation as a function of germination time.

NPT II Enzyme Activity

NPT II enzyme activity is detected by a standard in situ gel assay. Briefly, 100 mg. of a leaf tissue was mixed with 20 ml. of extraction buffer in a 1.5 ml. Eppendorf tube. Tissue samples are macerated with a Konte pestle and centrifuged for 20 minutes at 4° C. A 35 $\mu$l aliquot of the supernatant solutions was electrophoresed on a non-denaturing 10% polyacrylamide gel. The gel was overlaid with a 1% agarose gel containing 67 mM. tris-maleate (pH 7.1), 42 mM. $MgCl_2$, 400 mM $NH_4Cl$, 20 $\mu$g kanamycin sulfate and 200 $\mu$Ci $\gamma$-[$^{32}$P]ATP. After incubating for 30 minutes at room temperature, the agarose gel is blotted onto Whatman P81 phosphocellulose paper overnight. The P81 paper is removed, washed several times with hot water (80° C.) and autoradiographed.

To practice the present invention, various techniques well known to those skilled in the art for manipulation of Agrobacterium strains and plasmids (virulent, non-virulent, cis- or trans- configurations) are employed. Enzymes are obtained from commercial sources and are used according to the vendor's recommendations or other variations known to the art. Reagents, buffers and culture conditions are also known to those in the art. General references containing such standard techniques include the following: R. Wu, ed. (1979) *Meth. Enzymol.* Vol. 68; J. H. Miller (1972) *Experiments in Molecular Genetics*; T. Maniatis et al. (1982) *Molecular Cloning; A Laboratory Manual*; and D. M. Glover, ed. (1985) *DNA Cloning* Vol. II, all of which are incorporated by reference.

Recently an alternative approach for the transfer and integration of DNA into a plant genome has been developed (Klein, T. M. et al., (1987) Nature 327:70–73). This technique relies on the use of microprojectiles on which the DNA (plasmid form) is attached. These microprojectiles are accelerated to high velocities and their momentum is used to penetrate plant cell walls and membranes. After penetration into a plant cell the attached DNA leaches off the microprojectile and is transferred to the nucleus where DNA repair enzymes integrate the "free" DNA into the plant genome. In its present form the process is entirely random, but plant tissues which have been successfully transformed by the plasmid DNA (or part of it) can be identified and cultured to homogeneity by the use of selectable marker genes (such as the bacterial neomycin phosphotransferase II gene, NPTII), or reporter genes (such as the bacterial beta-glucuronidase gene, Gus). Successful use of particle acceleration to transform plants has been shown for many plants including soybean. Plasmid pGA482/G/CPTEVPRV (Chart 9) can also be used for microprojectile transfer as it already has both the NPTII and Gus genes attached to the TEV PRV cassette.

Example 2

Construction of a Multigene containing the tobacco etch virus protease gene, the human renin gene, and the human tPA gene under the control of the SV40 promoter.

This example describes a multigene which has the TEV protease and two human structural genes under the control of Simian Virus 40 (SV40) promoter. Using the SV40 promoter, multigenes of this construction may be used for expression in animal systems, either cellular or in transgenic animals. The SV40 promoter is widely used in animal expression systems (Moreau et al, 1981 Nuc. Acids Res. 9:6047–68). The multigene construction described in this example is useful for the expression of cDNA clones of both human renin (Imai et al, 1983 Proc. Natl. Acad. Sci. USA 80:7405–9) and human tissue plasminogen activator (tPA) (Pennica et al, Nature 301:214–21).

As in, CPCR technology is used in this example to add restriction endonuclease sites to the 5′ and 3′ ends of copies of genes to be incorporated into the multigene construction of this example.

The first step in this construction is to use CPCR technology to amplify SV40 promoter and add appropriate restriction enzyme sites at the 5′ and 3′ ends (see Chart 4). Selection of restriction enzyme sites can be adjusted to avoid sites internal to any of the particular genes which are to be used in the multigene. The copies are generated from wildtype SV40 DNA. The 5′ oligomer used to amplify the SV40 promoter adds an EcoRI site to the 5′ end. The 3′ oligomer used in the amplification adds an NcoI site at the initiation codon at the 3′ end. The resulting fragment, referred to as $P_{sv}$ fragment in Chart 4 contains a copy of the SV40 promoter with an EcoRI site at its 5′ end and an EcoRI site and a NcoI site at the 3′ end downstream from the initiation codon. The following oligomer primers are used to generate $P_{sv}$ fragment:

5′ primer 5′-TACTTAAGAATTCGGAAGACTCCGCCTTTCTTGG-3′
and
3′ primer 5′-AATCCAACCATGGGAAACGTTTCGAAAAACGTTTTCGG-3′.

The TEV protease gene is amplified from TEVDNA using oligomer primers which are designed to add an NcoI site to the 5′ end and the restriction enzyme sites KpnI and EcoRI to the 3′ end. The resulting fragment, referred to as TEV protease fragment in Chart 4 contains a copy of the TEV protease gene with an NcoI site at the 5′ end and a KpnI site and a EcoRI site at the 3′ end downstream from the PSJ. The following oligomers are used to generate TEV protease fragment:

5′ primer 5′-ATCGATTCCATGGGGAAGAAGAATCAGAAGCACAAGC-3′
and
3′ primer 5′-ATCATTGAATTCGGTACCCTTCTCCCCTTGCGAGTACACC-3′.

The amplified SV40 promoter (400 bp) and TEV protease (1300 bp) fragments are then treated with NcoI and ligated to each other. The resulting 1700 bp fragment, referred to as $P_{sv}$/TEV fragment in Chart 4, is treated with EcoRI and inserted into the plasmid pUC18 which is opened with EcoRI. The resulting recombinant plasmid is referred to as pUC18SVTEV and shown in Chart 4. This plasmid contains an inframe KpnI site in the SVTEV insert which can be used to clone additional genes.

In order to clone additional genes into the construction and have them expressed and cleaved in a multi-gene system, a PSJ must be inserted between any genes which are added. A vector, pUC18PSJ, was developed which can be used to achieve this goal. Using pUC18PSJ, two genes may be cloned, one 5' of an inframe PSJ and the other 3' inframe of the PSJ. The particular vector described here encodes inframe KpnI sites at its 5' and 3' ends. The PSJ of pUC18PSJ is an amplified copy of the PSJ found between the TEV protease and 54 kdalton nuclear inclusion protein genes of the TEV genome. Downstream adjacent to the 5' KpnI site and upstream from the PSJ is located in inframe BglII site. The CPCR produced copy additionally contains upstream adjacent to the 3' KpnI site downstream from the PSJ, an inframe HindIII site. This construction, shown in Chart 5 and referred to as TEVPSJ fragment, is synthesized directly using a DNA synthesizing instrument. The following oligomer is synthesized: 5'-GGTACCAGATCTAATGAAC-CAGTCTATTTCCAAGGGAAGAAGCTTG-GTACCC-3'. The complementary strand of this oligomer is also synthesized and the resulting DNA fragment is TEVPSJ fragment, the TEV PSJ with a a KpnI site and a BglIIsite upstream from the PSJ sequence and a HindIII site and a KpnI site downstream from the PSJ sequence.

The amplified PSJ with the additional restriction enzyme sites added to its 5' and 3' end is treated with KpnI and cloned into pUC18 which is cut with KpnI. The vector pUC18PSJ is formed and shown in Chart 5.

In this example, both human renin and human tPA genes are cloned into pUC18PSJ. This construction requires two steps. First, the gene for human renin gene is amplified from a copy of the human renin gene using CPCR technology. Inframe BglII sites are added at the 5' and 3' end. Depicted in Chart 6, the resulting fragment is shown and referred to as human renin insert. The following oligomer primers are used to produce the human renin insert:

5' primer 5'-ATTCCTAGATCTCTGACACTTGGCAACACCACCTC-3'
and
3' primer 5'-AATTAAAGATCTGCGGGCCAAGGCGAAGCCAATGC-3'.

The amplified human renin gene with BglII sites at its 5' and 3' ends is then cloned into the BglII site located upstream from the PSJ in pUC18PSJ, forming plasmid pUC18RenPSJ.

The human tPA gene is also amplified from a copy of the human gene using CPCR technology. In the amplified gene, a HindIII site has been added at the 5' end and a HindIII site is added at the 3' end of the human tPA gene after the polyadenylation signal of that gene. This is shown in Chart 6; the resulting fragment is referred to as human tPA insert. The following oligomers are used to amplify the tPA:

5' primer 5'-AATTTAAAGCTTGCCAGATCTTACCAAGTGATCTGC-3'
and
3' primer 5'-AATGCTAAGCTTGGAAAAAACTGTGAAAAAATATATCC-3'.

This amplified gene with a HindIII sites at this 3' and 5' end, human tPA insert, is cloned into the HindIII site located downstream from the PSJ in pUC18RenPSJ. The resulting plasmid, pUC18RenPSJtPA is then digested with KpnI and the fragment containing the renin gene linked 5' to the PSJ which is linked 3' to the tPA gene is isolated. This fragment, shown in Chart 7 as RenPSJtPA fragment, is then ligated into the KpnI site of pUC18SVTEV to form plasmid pUC18SVTEV-RenPSJtPA.

Example 3

Multigene construct for expression in prokaryotes

The following example illustrates a construction which can be used to express in a bacterial expression system, such as $E.\ coli$ a multigene which contains a protease. This construction follows directly from Example 2 which describes the major elements needed except that instead of using the SV40 promoter, a bacterial promoter is used. In this example the $\lambda$ phage $P_L$ promoter is used. The $P_L$ promoter can be obtained from any number of $E.\ coli$ expression vectors or from the $\lambda$ phage DNA. In this example, an EcoRI site to the 5'-end and an NcoI site to the 3'-end of the promoter by CPCR technology to form $P_L$ fragment as shown in Chart 8. The following oligomer primers are used:

5' primer 5'-ATAATTGAATTCCATACAGATAACCATCTGCGGTG-3'
and
3' primer 5'-AATACACCATGGTATCGATATACCTCCTTAATTTTAA-3'

After CPCR amplification, the 120 bp $P_L$ promoter fragment is subjected to digestion with NcoI and ligated with the 1 kb TEV protease gene containing fragment referred to as TEV protease fragment described in Example 2. The product of this ligation, referred to as $P_L$TEV fragment in Chart 8, is then digested with EcoRI and cloned into pUC18 to obtain the plasmid referred to as pUC18$P_L$TEV in Chart 8. As described in Example 2, the TEV protease fragment which is incorporated in the vector pUC18$P_L$TEV contains an inframe KpnI site which can be used as a cloning site. The multigene construction RenPSJtPA fragment which was described in Example 2 and shown in Chart 7 can be inserted in the KpnI site of pUC18$P_L$TEV. The clone resulting from the addition of the $P_L$ promoter to the human renin and tPA genes is referred to as pUC18$P_L$TEVRentPA and shown in Chart 8.

A host bacteria can be transformed with plasmid pUC18$P_L$TEVRentPA and the multigene will be expressed. The translation product will be processed by the TEV protein and both human renin and human tPA will be produced by the transformed bacteria.

Example 4

Expression of a multigene in a eukaryotic host

Plasmid pSVTEVRentPA, described in Example 2, is digested with EcoR1 and the fragment containing the multigene under the regulatory control of the SV40 promoter is isolated. Chinese Hamster Ovary (CHO) cells are transfected with the multigene fragment. Cells are selected which express human renin and human tPA. The techniques used are widely known to those having ordinary skill in the art.

Example 5

Production of a transgenic animal using a recombinant multigene as the transgene Plasmid pSVTEVRentPA, described in Example 2, is digested with EcoR1 and the fragment containing the multigene under the regulatory control of the SV40 promoter is isolated. The recombinant multigene is introduced into non-human animal embryos using the methods described in Wagner, T.E. et al, Microinjection of a rabbit β-globin gene into zygotes and its subsequent expression in adult mice and their offspring. Proc. Natl. Acad. Sci. USA Vol. 78, No. 10 pp. 6376–6380, (Oct. 1981). Between 200 and 400 copies of the recombinant multigene are microinjected into each male pronuclei. Several lines of transgenic animals which express both human renin and human tPA are generated. The copy number for the multigene construct range between 5 to 10 copies per genome.

-continued
Chart 2

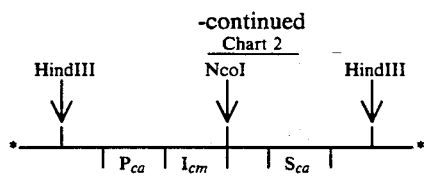

cp-exp fragment

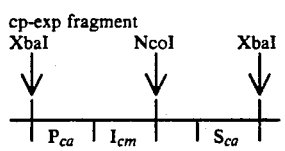

pUC18Xcp-exp

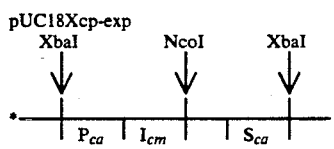

TEV

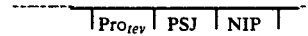

TEV protease fragment

pUC18pro-exp

Chart 1

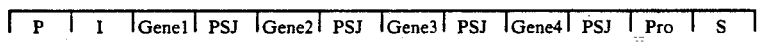

Chart 2 pUC18cp-exp

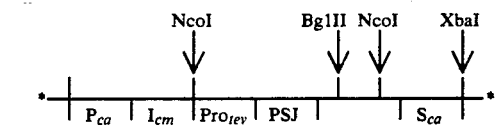

Chart 3

TEV

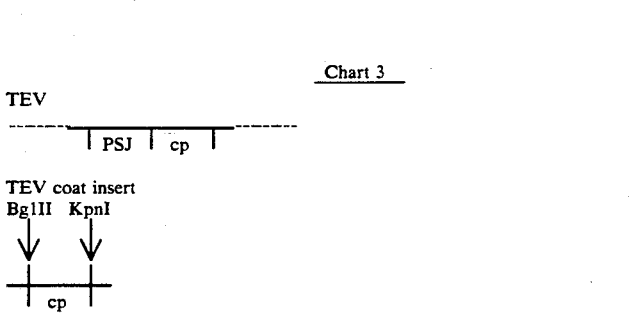

TEV coat insert

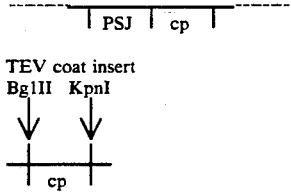

PRV

PRV coat insert

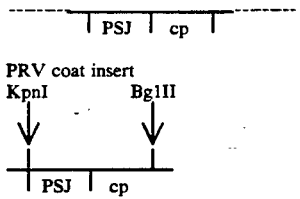

TEV/PRV coat fragment

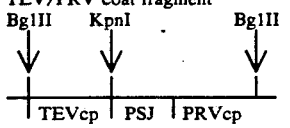

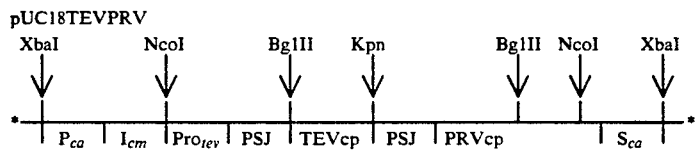
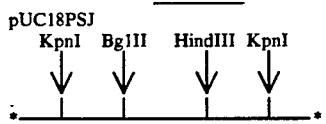
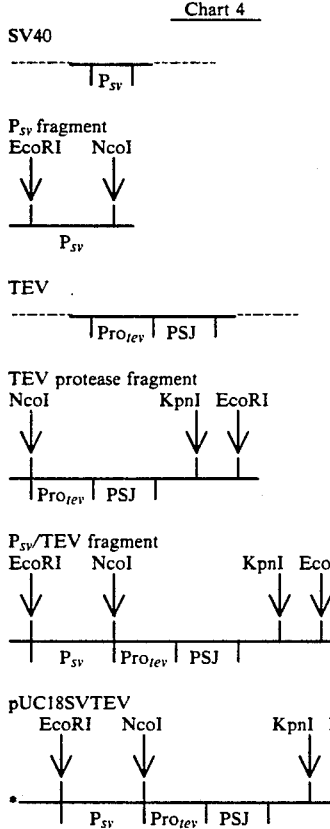
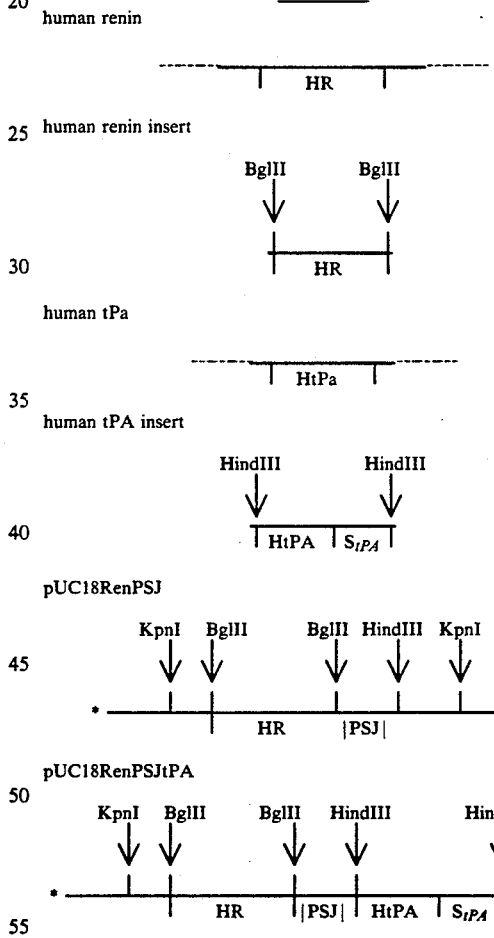
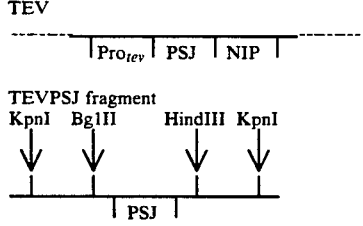
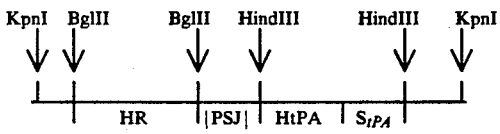

Chart 7
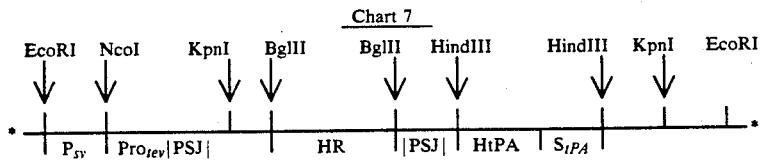
Chart 8
λ phage DNA
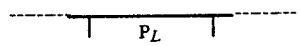
$P_L$ fragment
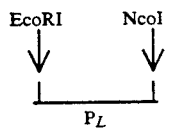
TEV protease fragment
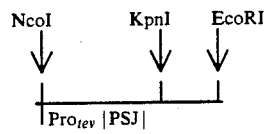
$P_L$TEV fragment
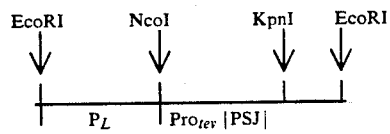
pUC18$P_L$TEV
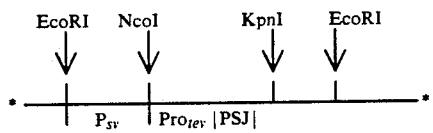
pUC18$P_L$TEVRentPA
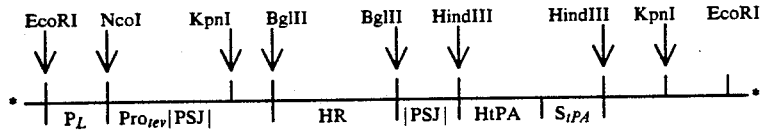
CHART 9
pGA482
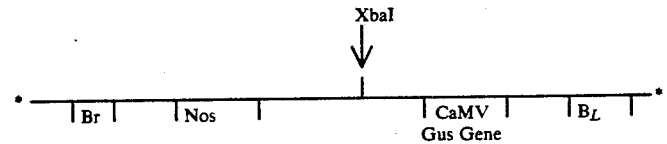
pGA482/G/CPTEVPRV -continued
CHART 9

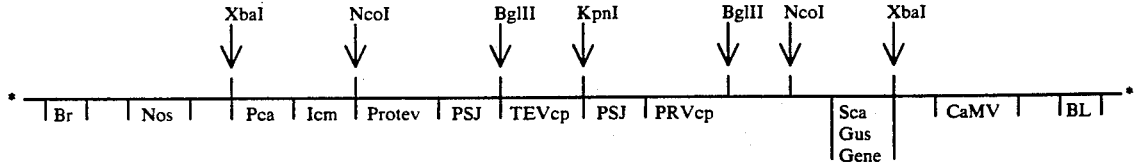

I claim:
1. A recombinant multigene vector comprising:
a) a plurality of structural genes; and
b) a plurality of DNA sequences which encode peptide linkers;
wherein at least one of said structural genes encodes a potyvirus protease;
DNA sequences adjacent to said structural genes are said DNA sequences which encode peptide linkers; and
said peptide linkers contain an amino acid sequence which said potyvirus protease recognizes as a protease cleavage site.

2. A recombinant multigene vector according to claim 1 wherein said potyvirus protease is selected from the group consisting of tobacco etch virus protease, watermelon mosaic virus 2 protease, zucchini yellow mosaic virus protease, and papaya ringspot 2 virus protease.

3. A recombinant multigene vector according to claim 1 wherein said peptide linker encodes the amino acid sequence selected from the group consisting of gln-gly, gln-ser, and gln-ala.

4. A recombinant multigene vector according to claim 1 wherein at least one of said structural genes is a potyvirus coat protein gene.

5. A recombinant multigene vector according to claim 4 wherein said potyvirus coat protein gene is selected from a group consisting of tobacco etch virus coat protein gene, watermelon mosaic virus 2 coat protein gene, zucchini yellow mosaic virus coat protein gene, and papaya ringspot 2 virus coat protein gene.

6. A recombinant multigene vector according to claim 5 wherein said linker encodes the amino acid sequence selected from the group consisting of gln-gly, gln-ser, and gln-ala.

7. A transformed host cell comprising a recombinant multigene vector, according to claim 1 wherein said host cell is a plant cell.

8. A transgenic plant comprising a recombinant multigene vector according to claim 1.

* * * * *